(12) United States Patent
Bachman

(10) Patent No.: US 9,314,242 B2
(45) Date of Patent: *Apr. 19, 2016

(54) SINGLE CATHETER HEART REPAIR DEVICE AND METHOD FOR USE

(71) Applicant: Edwards Lifesciences Corporation, Irvine, CA (US)

(72) Inventor: Alan B. Bachman, Milford, CT (US)

(73) Assignee: Edwards Lifesciences Corporation, Irvine, CA (US)

( * ) Notice: Subject to any disclaimer, the term of this patent is extended or adjusted under 35 U.S.C. 154(b) by 353 days.

This patent is subject to a terminal disclaimer.

(21) Appl. No.: 13/932,939

(22) Filed: Jul. 1, 2013

(65) Prior Publication Data

US 2013/0296894 A1  Nov. 7, 2013

Related U.S. Application Data

(63) Continuation of application No. 13/584,476, filed on Aug. 13, 2012, now Pat. No. 8,475,472, which is a continuation of application No. 13/027,045, filed on Feb. 14, 2011, now Pat. No. 8,241,304, which is a continuation of application No. 11/450,602, filed on Jun. 9, 2006, now Pat. No. 7,887,552, which is a continuation of application No. 10/233,879, filed on Sep. 3, 2002, now Pat. No. 7,083,628.

(51) Int. Cl.
*A61B 17/10* (2006.01)
*A61B 17/04* (2006.01)
*A61B 17/06* (2006.01)
*A61B 17/00* (2006.01)
*A61B 17/30* (2006.01)

(52) U.S. Cl.
CPC .......... *A61B 17/0401* (2013.01); *A61B 17/0469* (2013.01); *A61B 17/0482* (2013.01); *A61B 17/06166* (2013.01); *A61B 2017/00243* (2013.01); *A61B 2017/0472* (2013.01); *A61B 2017/306* (2013.01)

(58) Field of Classification Search
CPC .......... A61B 17/0401; A61B 17/0469; A61B 2017/306; A61B 2017/00243; A61B 17/06166; A61B 17/0482; A61B 2017/0472
See application file for complete search history.

(56) References Cited

U.S. PATENT DOCUMENTS

| | | |
|---|---|---|
| 3,769,980 A | 11/1973 | Karman |
| 3,805,793 A | 4/1974 | Wright |
| 4,055,167 A | 10/1977 | Bernstein |
| 4,311,140 A | 1/1982 | Bridgman |

(Continued)

FOREIGN PATENT DOCUMENTS

| | | |
|---|---|---|
| DE | 19725739 | 4/1999 |
| EP | 570915 | 11/1993 |

(Continued)

*Primary Examiner* — Julian W Woo

(57) ABSTRACT

A system and method for repairing a human heart uses a catheter with an extendable tip and multiple tissue fasteners. The catheter is advanced into a human heart with the extendable tip adjacent a first tissue portion. The extendable tip is extended to form a tissue-receiving opening, the first tissue portion is positioned within the tissue-receiving opening, and the extendable tip is withdrawn to mechanically hold the first tissue portion. A first tissue fastener is secured to the first tissue portion, which is then released from the tissue-receiving opening. A second tissue fastener may subsequently be passed through a second tissue portion.

18 Claims, 12 Drawing Sheets

(56) References Cited

U.S. PATENT DOCUMENTS

| | | |
|---|---|---|
| 4,350,160 A | 9/1982 | Kolesov et al. |
| 5,080,663 A | 1/1992 | Mills et al. |
| 5,242,456 A | 9/1993 | Nash et al. |
| 5,267,958 A | 12/1993 | Buckbinder et al. |
| 5,330,442 A | 7/1994 | Green et al. |
| 5,374,275 A | 12/1994 | Bradley et al. |
| 5,403,326 A | 4/1995 | Harrison et al. |
| 5,443,446 A | 8/1995 | Shturman |
| 5,458,131 A | 10/1995 | Wilk |
| 5,474,573 A | 12/1995 | Hatcher |
| 5,540,704 A | 7/1996 | Gordon et al. |
| 5,569,274 A | 10/1996 | Rapacki et al. |
| 5,573,540 A | 11/1996 | Yoon |
| 5,575,800 A | 11/1996 | Gordon |
| 5,578,044 A | 11/1996 | Gordon et al. |
| 5,601,574 A | 2/1997 | Stefanchik et al. |
| 5,609,598 A | 3/1997 | Laufer et al. |
| 5,643,289 A | 7/1997 | Sauer et al. |
| 5,662,664 A | 9/1997 | Gordon et al. |
| 5,685,867 A | 11/1997 | Twardowski et al. |
| 5,695,457 A | 12/1997 | St. Goar et al. |
| 5,695,504 A | 12/1997 | Gifford et al. |
| 5,700,272 A | 12/1997 | Gordon et al. |
| 5,713,910 A | 2/1998 | Gordon et al. |
| 5,713,911 A | 2/1998 | Racenet et al. |
| 5,716,367 A | 2/1998 | Koike et al. |
| 5,741,277 A | 4/1998 | Gordon et al. |
| 5,741,279 A | 4/1998 | Gordon et al. |
| 5,766,183 A | 6/1998 | Sauer |
| 5,769,863 A | 6/1998 | Garrison |
| 5,792,094 A | 8/1998 | Stevens et al. |
| 5,792,153 A | 8/1998 | Swain et al. |
| 5,810,847 A | 9/1998 | Laufer et al. |
| 5,814,097 A | 9/1998 | Sterman et al. |
| 5,836,956 A | 11/1998 | Buelna et al. |
| 5,839,639 A | 11/1998 | Sauer et al. |
| 5,840,030 A | 11/1998 | Ferek-Petric et al. |
| 5,849,019 A | 12/1998 | Yoon |
| 5,860,992 A | 1/1999 | Daniel et al. |
| 5,885,238 A | 3/1999 | Stevens et al. |
| 5,891,159 A | 4/1999 | Sherman et al. |
| 5,891,160 A | 4/1999 | Williamson et al. |
| 5,924,424 A | 7/1999 | Stevens et al. |
| 5,928,224 A | 7/1999 | Laufer |
| 5,928,250 A | 7/1999 | Koike et al. |
| 5,968,059 A | 10/1999 | Ellis et al. |
| 5,972,020 A | 10/1999 | Carpentier et al. |
| 5,976,159 A | 11/1999 | Bolduc et al. |
| 6,004,310 A | 12/1999 | Bardsley et al. |
| 6,010,531 A | 1/2000 | Donlon et al. |
| 6,015,417 A | 1/2000 | Reynolds, Jr. |
| 6,015,427 A | 1/2000 | Mueller et al. |
| 6,029,671 A | 2/2000 | Stevens et al. |
| 6,047,700 A | 4/2000 | Eggers et al. |
| 6,056,760 A | 5/2000 | Koike et al. |
| 6,080,182 A | 6/2000 | Shaw et al. |
| 6,083,219 A | 7/2000 | Laufer |
| 6,088,889 A | 7/2000 | Luther et al. |
| 6,117,159 A | 9/2000 | Huebsch et al. |
| 6,136,010 A | 10/2000 | Modesitt et al. |
| 6,149,660 A | 11/2000 | Laufer et al. |
| 6,157,852 A | 12/2000 | Selmon et al. |
| 6,162,233 A | 12/2000 | Williamson et al. |
| 6,165,183 A | 12/2000 | Kuehn et al. |
| 6,165,204 A | 12/2000 | Levinson et al. |
| 6,190,357 B1 | 2/2001 | Ferrari et al. |
| 6,210,419 B1 | 4/2001 | Mayenberger et al. |
| 6,234,995 B1 | 5/2001 | Peacock |
| 6,238,336 B1 | 5/2001 | Ouchi |
| 6,269,819 B1 | 8/2001 | Oz et al. |
| 6,312,447 B1 | 11/2001 | Grimes |
| 6,443,922 B1 | 9/2002 | Roberts et al. |
| 6,461,366 B1 | 10/2002 | Seguin |
| 6,464,707 B1 | 10/2002 | Bjerken et al. |
| 6,508,777 B1 | 1/2003 | Macoviak et al. |
| 6,551,330 B1 | 4/2003 | Bain et al. |
| 6,575,971 B2 | 6/2003 | Hauck et al. |
| 6,582,388 B1 | 6/2003 | Coleman et al. |
| 6,626,930 B1 | 9/2003 | Allen et al. |
| 6,629,534 B1 | 10/2003 | St. Goar et al. |
| 6,638,293 B1 | 10/2003 | Makower et al. |
| 6,641,592 B1 | 11/2003 | Sauer et al. |
| 6,645,205 B2 | 11/2003 | Ginn |
| 6,752,813 B2 | 6/2004 | Goldfarb et al. |
| 6,770,083 B2 | 8/2004 | Seguin |
| 6,860,890 B2 | 3/2005 | Bachman et al. |
| 6,875,224 B2 | 4/2005 | Grimes |
| 6,911,034 B2 | 6/2005 | Nobles et al. |
| 6,997,931 B2 | 2/2006 | Sauer et al. |
| 7,083,628 B2 | 8/2006 | Bachman |
| 7,094,244 B2 | 8/2006 | Schreck |
| 8,241,304 B2 * | 8/2012 | Bachman ............... 606/139 |
| 8,475,472 B2 * | 7/2013 | Bachman ............... 606/139 |
| 2002/0049402 A1 | 4/2002 | Peacock et al. |
| 2002/0107530 A1 | 8/2002 | Sauer et al. |
| 2002/0107531 A1 | 8/2002 | Schreck et al. |
| 2003/0130571 A1 | 7/2003 | Lattouf |
| 2003/0167062 A1 | 9/2003 | Gambale et al. |
| 2003/0167071 A1 | 9/2003 | Martin |
| 2003/0195524 A1 | 10/2003 | Barner |
| 2003/0208209 A1 | 11/2003 | Gambale |
| 2004/0044365 A1 | 3/2004 | Bachman |
| 2004/0049215 A1 | 3/2004 | Snow et al. |
| 2004/0068272 A1 | 4/2004 | Sauer et al. |
| 2004/0181238 A1 | 9/2004 | Zarbatany et al. |
| 2006/0004410 A1 | 1/2006 | Nobis et al. |
| 2006/0167338 A1 | 7/2006 | Schfaram |

FOREIGN PATENT DOCUMENTS

| | | |
|---|---|---|
| EP | 769272 | 4/1997 |
| EP | 861632 | 9/1998 |
| FR | 2768324 | 3/1999 |
| WO | WO 93/08738 | 5/1993 |
| WO | WO 95/15715 | 6/1995 |
| WO | WO 95/25468 | 9/1995 |
| WO | WO 97/13463 | 4/1997 |
| WO | WO 97/27807 | 8/1997 |
| WO | WO 97/27893 | 8/1997 |
| WO | WO 98/57585 | 12/1998 |
| WO | WO 99/00059 | 1/1999 |
| WO | WO 99/13777 | 3/1999 |
| WO | WO 99/15223 | 4/1999 |
| WO | WO 99/35980 | 7/1999 |
| WO | WO 00/03759 | 2/2000 |
| WO | WO 00/59382 | 10/2000 |
| WO | WO 00/60995 | 10/2000 |
| WO | WO 01/26557 | 4/2001 |
| WO | WO 01/28432 | 4/2001 |
| WO | WO 01/66018 | 9/2001 |
| WO | WO 01/95809 | 12/2001 |
| WO | WO 02/24078 | 3/2002 |
| WO | WO 02/34167 | 5/2002 |
| WO | WO 02/45598 | 6/2002 |
| WO | WO 03/001893 | 1/2003 |
| WO | WO 03/103536 | 12/2003 |
| WO | WO 2005/110244 | 11/2005 |

* cited by examiner

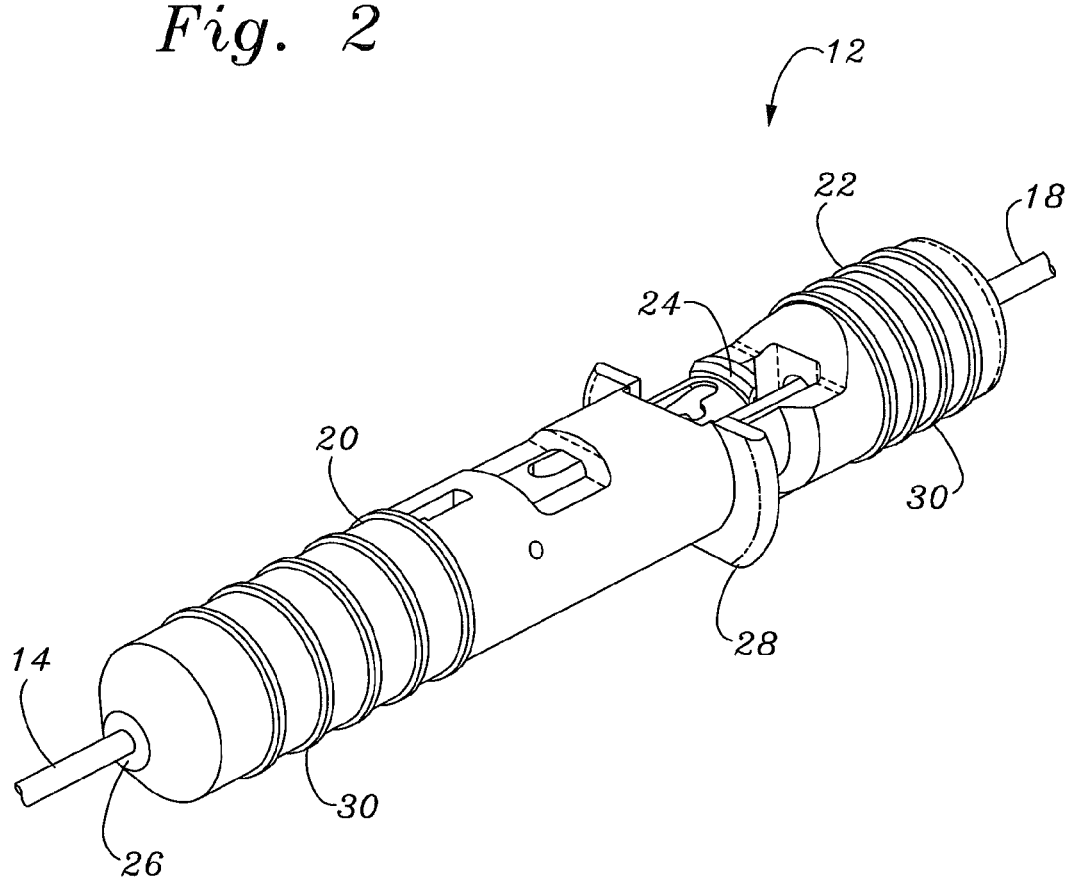

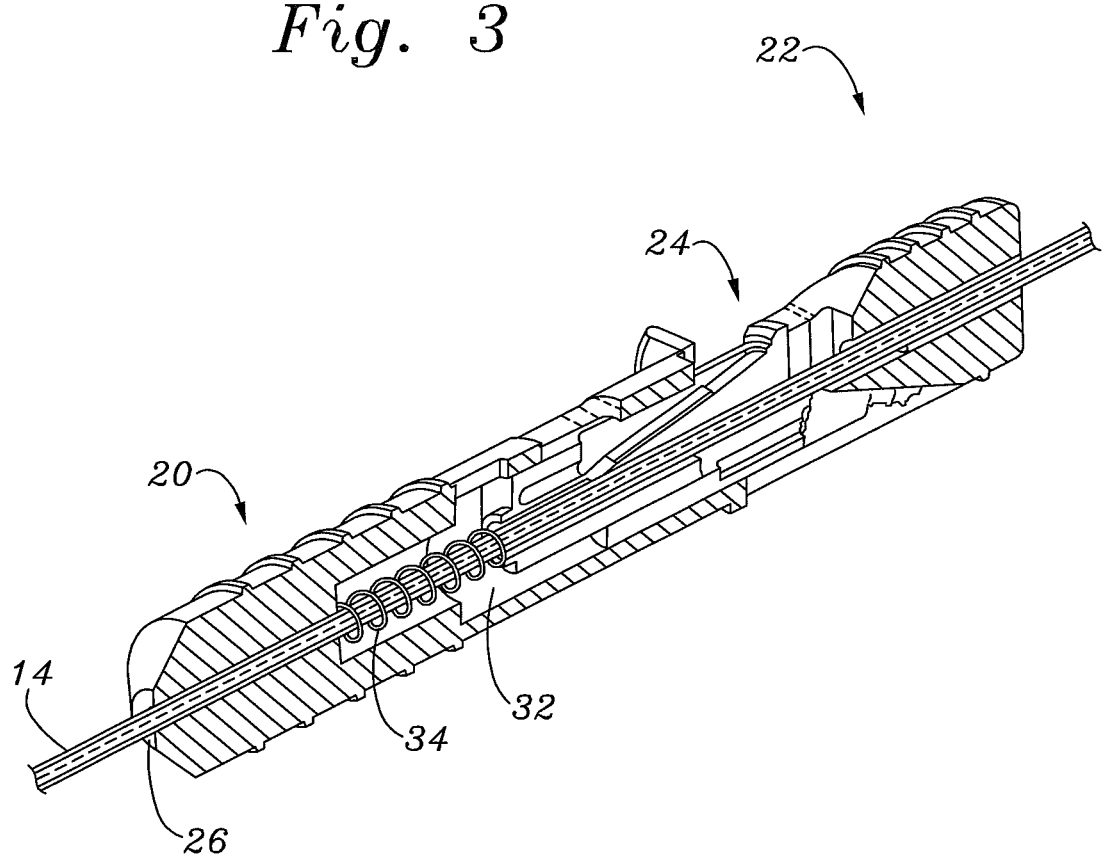

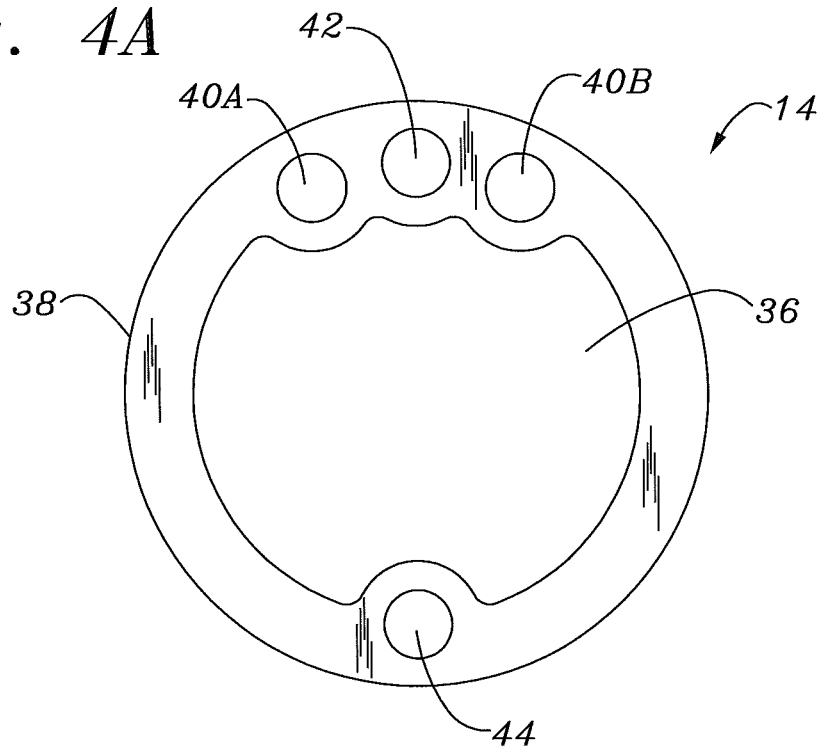
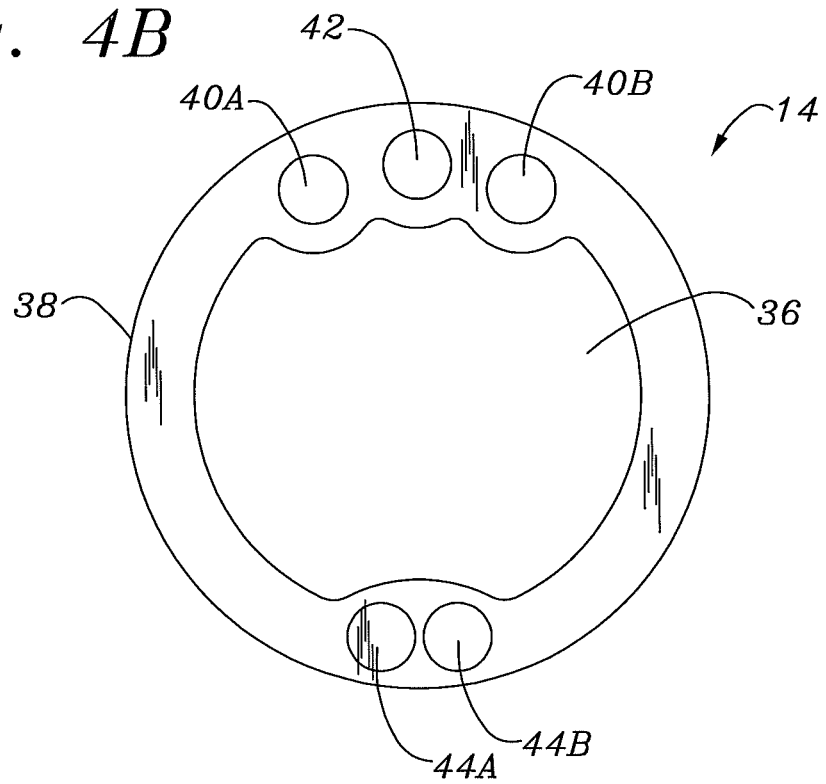

SINGLE CATHETER HEART REPAIR DEVICE AND METHOD FOR USE

CROSS REFERENCE TO RELATED APPLICATIONS

This application is a continuation of U.S. patent application Ser. No. 13/584,476, filed Aug. 13, 2012, entitled "Single Catheter Mitral Valve Repair Device and Method for Use," now U.S. Pat. No. 8,475,472, which is a continuation of U.S. patent application Ser. No. 13/027,045, filed Feb. 14, 2011, entitled "Single Catheter Mitral Valve Repair Device and Method for Use," now U.S. Pat. No. 8,241,304, which is a continuation of U.S. patent application Ser. No. 11/450,602, filed Jun. 9, 2006, entitled "Single Catheter Mitral Valve Repair Device and Method for Use," now U.S. Pat. No. 7,887,552, which is a continuation of U.S. patent application Ser. No. 10/233,879, filed Sep. 3, 2002, entitled "Single Catheter Mitral Valve Repair Device and Method for Use," now U.S. Pat. No. 7,083,628. This application discloses subject matter related to U.S. patent application Ser. No. 09/562,406, filed May 1, 2000, entitled "Minimally Invasive Mitral Valve Repair Method and Apparatus," now U.S. Pat. No. 6,626,930. The disclosures of all of the aforementioned United States patent applications are expressly incorporated herein by reference in their entirety.

BACKGROUND OF THE INVENTION

In vertebrate animals, the heart is a hollow muscular organ having four pumping chambers: the left atrium, the left ventricle, the right atrium and the right ventricle. The atria are isolated from their respective ventricles by one-way valves located at the respective atrial-ventricular junctions. These valves are identified as the mitral (or bicuspid) valve on the left side of the heart, and tricuspid valve on the right side of the heart. The exit valves from the left and right ventricles are identified as the aortic and pulmonary valves, respectively.

The valves of the heart are positioned in valvular annuluses that comprise dense fibrous rings attached either directly or indirectly to the atrial and ventricular muscle fibers. Valve leaflets comprising flexible collagenous structures are attached to, and extend inwardly from, the annuluses to meet at coapting edges. The aortic, tricuspid and pulmonary valves each have three leaflets, while the mitral valve only has two. In normal operation, the leaflets of the mitral valve open as left ventricle dilates thereby permitting blood to flow from the left atrium into the left ventricle. The leaflets then coapt (i.e. close) during the contraction cycle of the left ventricle, thereby preventing the blood from returning to the left atrium and forcing the blood to exit the left ventricle through the aortic valve. Similarly, the tricuspid valve regulates flow from the right atrium into the right ventricle, and the pulmonary valve regulates blood exiting the right ventricle.

For a number of clinical reasons various problems with heart valves can develop. One common form of heart disease involves the deterioration or degradation of the heart valves, which leads to stenosis and/or insufficiency. Heart valve stenosis is a condition in which the valve does not open properly. Insufficiency is a condition in which the valve does not close properly. Insufficiency of the mitral valve, most common because of the relatively high fluid pressures in the left ventricle, results in mitral valve regurgitation ("MR"), a condition in which blood reverses its intended course and flows "backward" from the left ventricle to the left atrium during heart contractions.

A number of surgical techniques have been developed to repair degraded or otherwise incompetent heart valves. A common procedure involves replacement of a native aortic or mitral valve with a prosthetic heart valve. Such procedures require the surgeon to access the heart through the patient's chest (or possibly percutaneously), surgically remove the incompetent native heart valve and associated tissue, remodel the surrounding valve annulus, and secure a replacement valve in the remodeled annulus. While these procedures can be very effective, there are associated shortcomings. For example, the highly invasive nature of the implantation procedure typically results in substantial patient discomfort and requires patients to remain hospitalized for extended recovery periods. In addition, the two basic types of commercially available replacement valves, mechanical valves, and tissue valves, have shortcomings of their own. Mechanical replacement valves typically offer extended operational lifetimes, but the patient is usually required to maintain a regimen of anti-coagulant drugs for the remainder of his or her life. Tissue valves typically offer a higher degree of acceptance by the body thereby reducing or eliminating the need for anti-coagulants, but the operational lifetimes of tissue valves is typically shorter than mechanical valves and thus may require a subsequent replacement(s).

As an alternative to prosthetic heart valve replacement, it is often preferable to remodel the native heart valve and/or surrounding tissue. Remodeling procedures often preserve left ventricular function better than mitral valve replacement because the subvalvular papillary muscles and chordae tendineae are preserved (most prosthetic valves do not utilize these muscles). Typically, valvular remodeling is accomplished by implanting a prosthetic ring ("annuloplasty ring") into the valve annulus to reduce and/or stabilize the structure of the annulus Annuloplasty rings are typically constructed of a resilient core covered with a fabric sewing material. Annuloplasty procedures can be performed alone, or they can be performed in conjunction with other procedures such as leaflet repair. Although annuloplasty procedures have become popular and well accepted, reshaping the surrounding annulus and traditional leaflet repairs do not always lead to optimum leaflet coaptation. As a result, some patients may still experience residual mitral valve regurgitation following annuloplasty procedures.

A recently developed technique known as a "bow-tie" repair has also been advocated for repairing insufficient heart valves, in particular the mitral valve. The mitral valve bow-tie technique involves, in its simplest form, suturing the anterior and posterior leaflets together near the middle of their coapting edges, thereby causing blood to flow through two newly formed side openings. While this does reduce the volume of blood that flows from the atrium to the ventricle, this loss is more than compensated by improved leaflet coaptation, which reduces mitral regurgitation. As originally developed by Dr. Ottavio Alfieri, this process involved arresting the heart, and placing the patient on extra corporeal bypass and required invasive surgery to access and suture the leaflets together. More recently, however, some have advocated a "beating heart" procedure in which the leaflets are accessed remotely and the heart remains active throughout the procedure.

A particular method for performing a beating heart bow-tie procedure (i.e. without extra corporeal bypass) has been proposed by Dr. Mehmet Oz, of Columbia University. The method and devices for performing the method are described in PCT publication WO 99/00059, published Jan. 7, 1999. In one embodiment of the disclosed procedure, the associated device consists of a forceps-like grasper used to grasp and hold the mitral valve leaflets in a coapted position for suturing. Since the mitral valve leaflets meet and curve toward and slightly into the left ventricular cavity at their mating edges, the grasper device is passed through a sealed aperture in the apex of the left ventricle. The edges of the mating mitral valve leaflets are then grasped and held together, and a fastening device such as a clip or suture is utilized to fasten them. The fastening device should be applied to the leaflet tissue with sufficient tissue purchase to prevent tear out or other failure, but close enough to the edges to ensure that the newly created side holes are as large as possible. The Mehmet Oz disclosure thus illustrates that teeth of the grasper device can be linearly slidable with respect to one another so as to permit alignment of the mitral valve leaflets prior to fastening. Since the procedure is done on a beating heart, it will be readily understood that the pressures and motions within the left ventricle and mitral valve leaflets are severe. Thus the procedure taught by Dr. Mehmet Oz is very skill-intensive.

The bow-tie technique has proved to be a viable alternative for treating otherwise incompetent heart valves. Nonetheless, several shortcomings associated with current bow-tie procedures have been identified. Current systems include devices having mechanical graspers, barbed members, and vacuum devices that simultaneously capture and retain the valve leaflets prior to applying a fastening device thereto. Often, use of these devices results in the less than optimal leaflet stabilization and fastener placement. Many of these problems arise from the fact that the surgeon is required to capture, retain and fasten the leaflets in one relatively inflexible procedure. These difficulties are compounded when the leaflets are small or calcified making them difficult to pull together, and in beating heart procedures in which the leaflets are actively functioning throughout the surgery. In light of the foregoing, there is presently a need for improved systems for stabilizing multiple tissue heart valve leaflets and placing a fastening device there between. More specifically, there is a present need for an improved bow-tie procedure for repairing a patient's mitral valve.

BRIEF SUMMARY OF THE INVENTION

The single catheter mitral valve repair device of the present invention may be used to repair tissue throughout a patient's body. However, it is particularly useful in repairing dysfunctional mitral valve tissue by stabilizing discreet valvular tissue pieces and deploying a fastening device therethrough, thereby coapting the tissue pieces. The present invention may also be used to repair arterial septal defects (ASD), ventricular septal defects (VSD), and defects associated with patent foramen ovale (PFO).

In one aspect, the repair device of the present invention comprises an extendable engagement tip having at least one port formed thereon, at least one deployable fastener in communication with the engagement tip, and one or more actuator members in communication with the port(s). The deployable fastener is capable of controllably engaging and fastening tissue located proximal to the engagement tip.

In another aspect of the present invention, the repair device comprises a handle, an elongated body, and an extendable engagement tip. The handle comprises a stationary handle body, an engagement tip actuator in communication with the stationary handle body, a fastener deployment housing in communication with the stationary handle body, and a vacuum connector capable of placing a vacuum source in communication with the stationary handle body. The elongated body comprises a flexible body member, at least one vacuum lumen, one or more actuation lumens and one or more fastener lumens. Optionally, the elongated body can also comprise one or more auxiliary lumens. The one or more actuation lumens are capable of receiving one or more actuation members therein. Similarly, the one or more fastener lumens are capable of receiving at least one deployable fastener therein. The extendable engagement tip comprises a fastener deployment housing capable of attaching to the elongated body, an actuation flange attached to the fastener deployment housing, an extendable tip attached to the actuation flange and in communication with the engagement tip actuator, a vacuum port in communication with the vacuum connector, and at least one deployable fastener in communication with the fastener deployment housing.

The present invention also discloses a method of repairing tissue using the repair device of the present invention and comprises grasping a first tissue portion with a vacuum force, stabilizing the first tissue portion with a mechanical force, deploying a tissue fastener into the stabilized first tissue portion, disengaging the first tissue portion, grasping at least a second tissue portion with a vacuum force, stabilizing at least a second tissue portion with a mechanical force, deploying at least a second tissue fastener into at least the second stabilized tissue portion, disengaging at least the second tissue portion, and coapting the first tissue portion and at least the second tissue portion with the first tissue fastener and at least the second tissue fastener.

Other objects, features, and advantages of the present invention will become apparent from a consideration of the following detailed description.

BRIEF DESCRIPTION OF THE DRAWINGS

The apparatus of the present invention will be explained in more detail by way of the accompanying drawings, wherein:

FIG. 2 shows a perspective view of the handle portion of the mitral valve repair device of the present invention;

FIG. 3 shows a cross-sectional view of the handle portion of the mitral valve repair device of the present invention;

FIGS. 4A and 4B show alternate cross-sectional views of the elongated body of the mitral valve repair device of the present invention;

DESCRIPTION OF THE PREFERRED EMBODIMENTS

Disclosed herein is a detailed description of various embodiments of the present invention. This description is not to be taken in a limiting sense, but is made merely for the purpose of illustrating the general principles of the invention. The overall organization of the description is for the purpose of clarity only and is not intended to limit the present invention.

The single catheter mitral valve repair device of the present invention is designed for use in a surgical treatment of bodily tissue. As those skilled in the art will appreciate, the exemplary single catheter mitral repair device disclosed herein is designed to minimize trauma to the patient before, during, and after a minimally invasive surgical procedure while providing improved tissue stabilization and enhanced placement of a fastening device thereon. While the single catheter mitral valve repair device of the present invention may be used to repair tissue throughout a patient's body, it is particularly useful in repairing dysfunctional mitral valve tissue by stabilizing discreet valvular tissue pieces and deploying a fastening device therethrough, thereby coapting the tissue pieces. The present invention may also be used to repair arterial septal defects (ASD), ventricular septal defects (VSD), and defects associated with patent foramen ovale (PFO).

Figure 1:
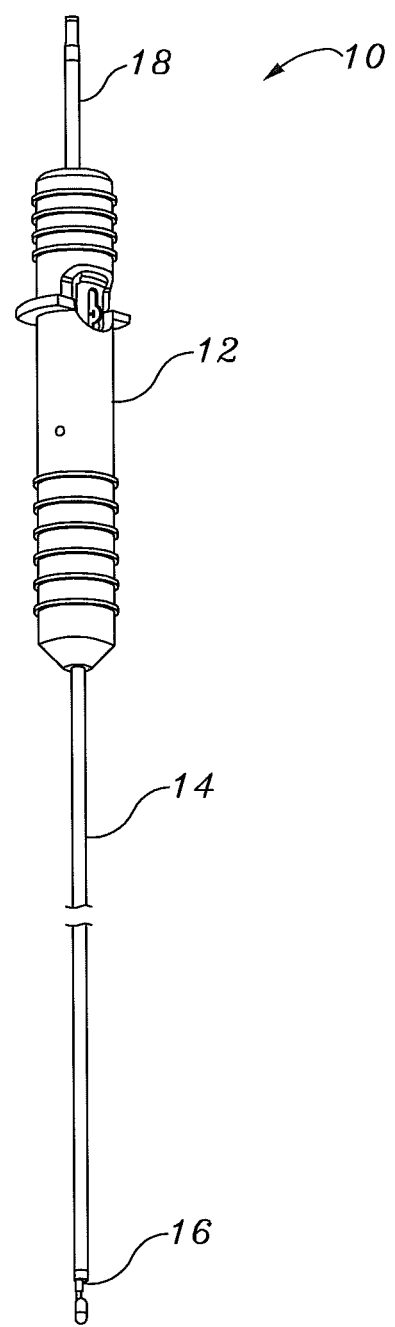
FIG. 1 shows a perspective view of the mitral valve repair device of the present invention.

FIG. 1 shows the single catheter mitral valve repair device of the present invention. As shown, the repair device 10 comprises a handle portion 12 attached to an elongated body 14. An engagement tip 16 is positioned on the distal portion of the elongated body 14. A vacuum connector 18 is attached to the handle 12. As those skilled in the art will appreciate, the present invention may be manufactured from a variety of materials including, without limitation, various metals, plastics, thermoplastics, silicones, elastomers, ceramics, composite materials, or various combinations of the aforementioned materials. For example, the handle 12 may be manufactured from polyethylene, while the elongated body 14 is manufactured by an elastomer. In an alternate embodiment the elongated body 14, the engagement tip 16, or both may incorporate radio-opaque or echogenic materials, thereby enabling the surgeon to precisely position the repair device 10 within the patient's body.

FIG. 2 shows a perspective view of the handle 12 of the present invention. As shown in FIG. 2, the handle 12 comprises a stationary handle body 20 having a tip actuator 22 and a fastener deployment actuator 24 in communication therewith. The tip actuator 22 and fastener deployment actuator 24 are movable relative to the stationary handle body 20. Exemplary tip actuator members or fastener deployment housings may include, for example, buttons, levers, slidable fixtures, or toggles. The distal portion of the stationary handle body 20 includes a coupling orifice 26 capable of receiving the elongated body 14 therein. In addition, the stationary handle body 20 may include a handle flange 28 located thereon. The stationary handle body 20, fastener deployment actuator 24, or tip actuator 22, may include at least one grip member 30 positioned thereon. As shown in FIG. 2, a vacuum connector 18 is in communication with the handle 12.

FIG. 3 shows a cross sectional view of the handle 12 of the present invention. As shown in FIG. 3, the stationary handle body 20 defines an actuation channel 32, which is in communication with the coupling orifice 26 formed on the distal portion of the stationary handle body 20. The actuation channel 32 formed inside the stationary handle body 20 is capable of receiving the tip actuator 22 and the fastener deployment actuator 24 independently and in telescoping relation therein. Those skilled in the art will appreciate that the present invention permits a user to actuate the tip actuator 22 or the fastener deployment actuator 24 independently. As shown, a bias member 34 may be positioned within the actuation channel 32 and may communicate in biasing relation with the fastener deployment actuator 24. The tip actuator 22 is in communication with at least one actuator extension member (see FIG. 7) positioned within one or more actuation lumens (see FIG. 4) formed in the elongated body 14. Similarly, the fastener deployment actuator 24 is in communication with at least one fastener extension member (see FIG. 6) positioned within one or more fastener lumens (see FIG. 4) formed in the elongated body 14. The vacuum connector 18 is to be connected to an external vacuum source and is in fluid communication with the vacuum lumen 36 formed in the elongated body 14.

The elongated body 14 of the present invention may be manufactured in a variety of lengths or diameters as desired by the user. FIGS. 4A and 4B show cross-sectional views of two embodiments of the elongated body 14 of the present invention. As shown in FIG. 4, the elongated body 14 of the present invention may comprise at least one vacuum lumen 36. In the illustrated embodiment, the vacuum lumen 36 is disposed in the center of the device; although those skilled in the art will appreciate that the present invention may be easily manufactured with the vacuum lumen 36 positioned at various locations within or alongside the elongated body 14. The body member 38 may further include one or more tip actuation lumens 40a, 40b, one or more auxiliary lumens 42, and one or more fastener lumens 44 formed therein. For example, FIG. 4B shows an alternate embodiment of the present invention wherein the body member 38 forms a vacuum lumen 36, tip actuation lumens 40a, 40b, auxiliary lumens 42, and two fastener lumens 44a, 44b therein. Those skilled in the art will appreciate that the one or more auxiliary lumens 42 of the present invention are capable of receiving a guidewire, thereby enabling the present invention to be directed to an area of interest in vivo with a guidewire. The elongated body 14 of the present invention may be attached to the handle 12 in a variety of manners, including, for example, adhesively attached or in snap-fit relation.

Figure 5A:
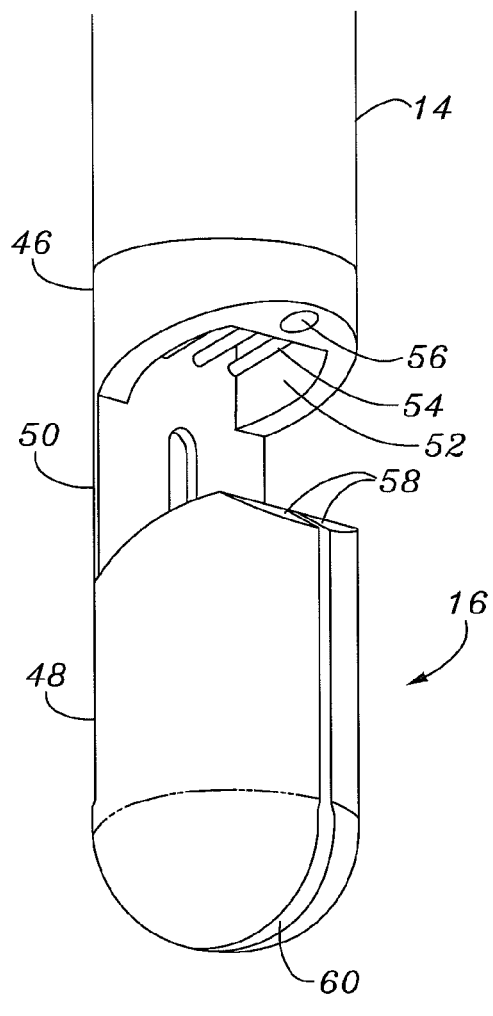
FIGS. 5A and 5B show alternate perspective views of the engagement tip of the mitral valve repair device of the present invention.

FIG. 5A shows a perspective view of the engagement tip 16 attached to the elongated body 14 of the present invention. The engagement tip 16 comprises a fastener deployment housing 46, an extendable tip 48, and an actuation flange 50 in communication with the fastener deployment housing 46 and the extendable tip 48. The fastener deployment housing 46 further includes at least one vacuum port 52 having a tissue support 54 located therein, and a fastener deployment port 56 located thereon. The tissue support 54 may comprise a series of vanes or other supports positioned across or proximate to the vacuum port 52. The vacuum port 52, positioned on the fastener deployment housing 46, is in fluid communication with the vacuum connector 18 positioned on the handle 12 through the vacuum lumen 36 formed in the elongated body 14. Similarly, the fastener deployment port 56 is in communication with the fastener deployment actuator 24 located on the handle 12 through fastener lumen 44 formed in the elongated body 14. In an alternate embodiment illustrated in FIG. 5B, a plurality of fastener deployment ports 56 may be formed on the fastener deployment housing 46 and may be in communication with a plurality of fastener lumens 44 formed in the elongated body 14 (see FIG. 4B). The extendable tip 48 of the present invention is in communication with the tip actuator 22 located on the handle 12 through the actuation lumens 40a, 40b formed in the elongated body 14. The extendable tip 48 may include a fastener receiver port 58 capable of receiving the deployable tight 64 therein (see FIG. 6). The fastener receiver port 58 is coaligned with or positioned proximate to the fastener deployment port 56 formed on the fastener deployment housing 46. The fastener receiving port 58 is capable of receiving the deployable needle 64 therein and includes a needle catch 68 attached to fastener material 62 (see FIG. 6). The needle catch 68 may comprise a variety of devices capable of engaging and retaining the deployable needle 64 therein, including, for example, a ferruled or sized ring. In addition, the extendable tip 48 may include a fastener channel 60 capable of receiving fastener material 62 therein. Preferably the fastener channel 60 is open on the distal end of extendable tip 48, as illustrated. Exemplary fastener materials include, for example, thread, wire, monofilament, braided filament, suture material, needles, sutures, staples, buttons, tissue-graspers, tissue clasps, barbs, and other tissue-coaption devices.

Figure 6:
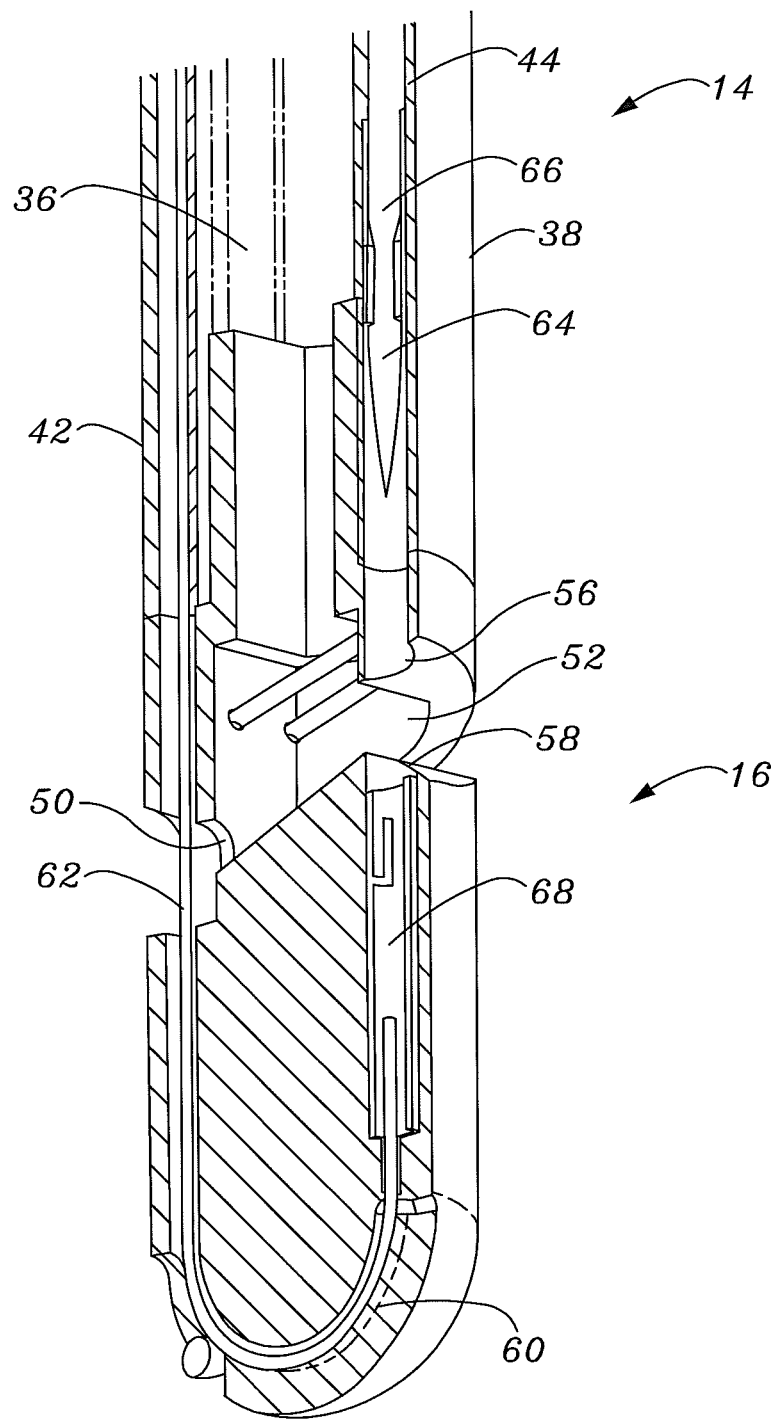
FIG. 6 shows a cross-sectional view of the engagement tip of the mitral valve repair device of the present invention.

FIG. 6 shows a cross sectional view of the engagement tip 16. The vacuum port 52 is in fluid communication with the vacuum lumen 36. A deployable needle 64 is in communication with the deployment housing 66 positioned within the fastener lumen 44. The receiver port 58 is in communication with the auxiliary lumen 42 located in the elongated body 14. A needle catch 68, which is capable of engaging and retaining the deployable needle 64, is attached to fastener material 62 which is positioned within the receiver port 58 and which extends through the auxiliary lumen 42 around the distal end of the engagement tip 16 and back towards the handle 12.

Figure 7A:
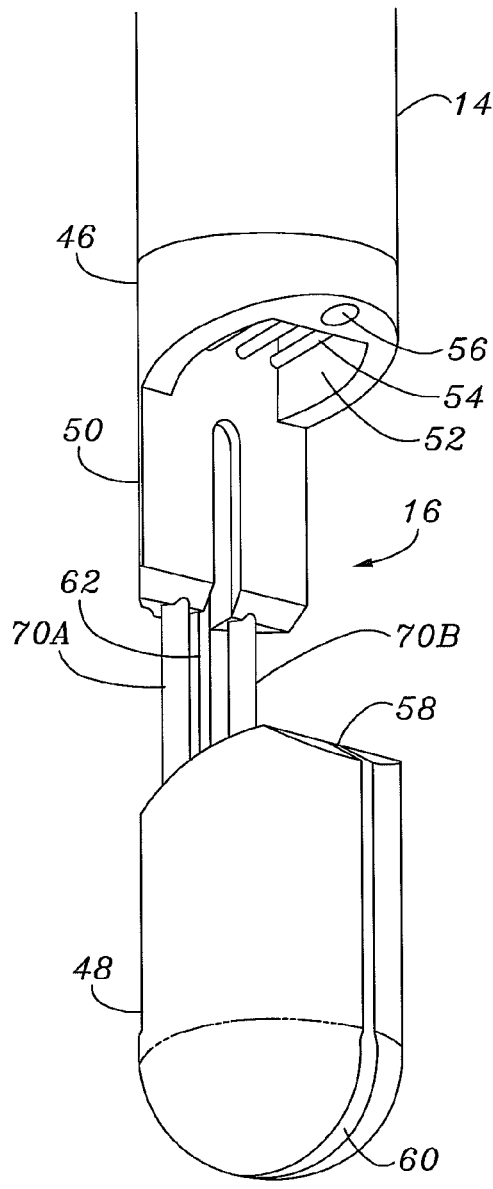
FIGS. 7A and 7B show alternate perspective views of the engagement tip of the mitral valve repair device of the present invention in an extended position.
Figure 7B:
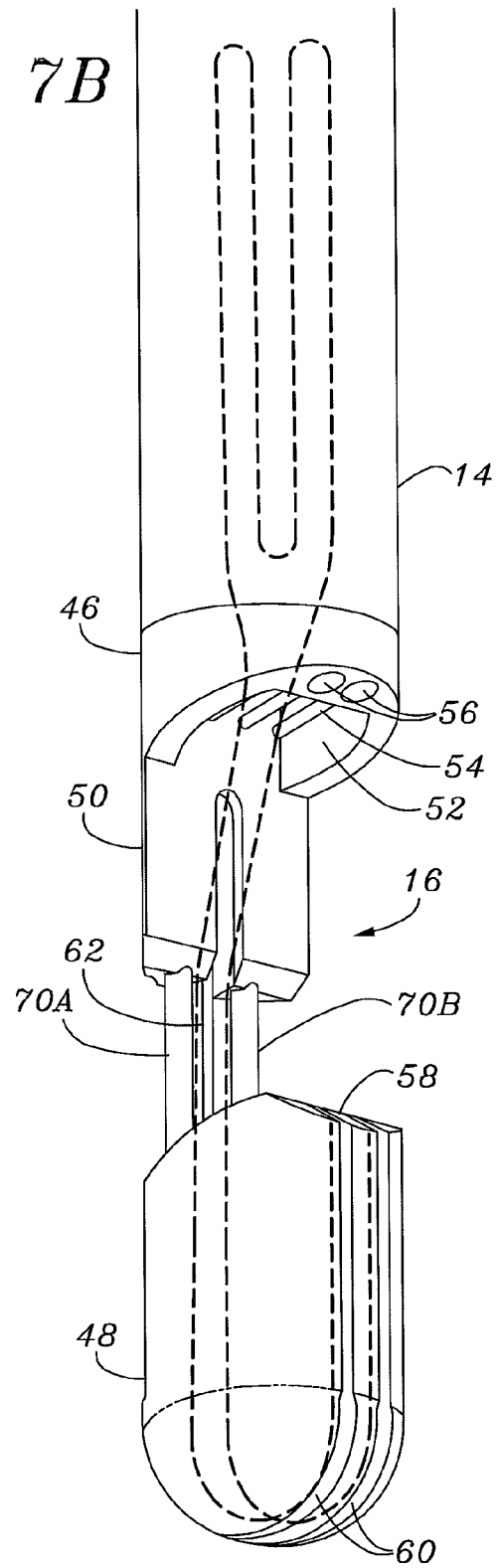

FIGS. 7A and 7B show the engagement tip 16 of the present invention in an extended configuration, thereby enabling the present invention to grasp and stabilize tissue located proximate thereto with a vacuum force. As shown in FIG. 7A, actuation members 70a, 70b are slidably received in the fastener deployment housing 46 and the extendable tip 48, thereby permitting the extendable tip 48 to be moved, in telescoping relation, relative to the fastener deployment housing 46. Exemplary actuation members 70a, 70b may include, for example, rods, shafts, or conduits. The actuation members 70a, 70b communicate with the tip actuator 22 positioned on the handle 12 through the actuation lumens 40a, 40b positioned in the elongated body 14. To actuate the extendable tip 48, the user advances the tip actuator 22 towards the stationary handle body 20, thereby advancing the actuation members 70a, 70b and resulting in the extendible tip 48 extending from the fastener deployment housing 46. To retract the extendible tip 48, the user retracts the tip actuator 22 away from the stationary handle body 20, thereby retracting the actuation members 70a, 70b and resulting in the extendible tip 48 retracting towards the fastener deployment housing 46. Those skilled in the art will appreciated that actuation of the tip actuator 22 results in the longitudinal movement of the actuation member 70a, 70b positioned in the tip actuator lumens 40a, 40b of the elongated body 14, thereby resulting in the longitudinal extension and retraction of the extendable tip 48. FIG. 7B shows and alternate embodiment in which there are a plurality (two in the illustrated case) of deployment ports 56, fastener receiver ports 58 and corresponding fastener channels 60. FIG. 7B illustrates another alternate embodiment in which the faster material is stored within the vacuum lumen 36 (as opposed to the auxiliary lumen 42, see FIG. 6).

Figure 8:
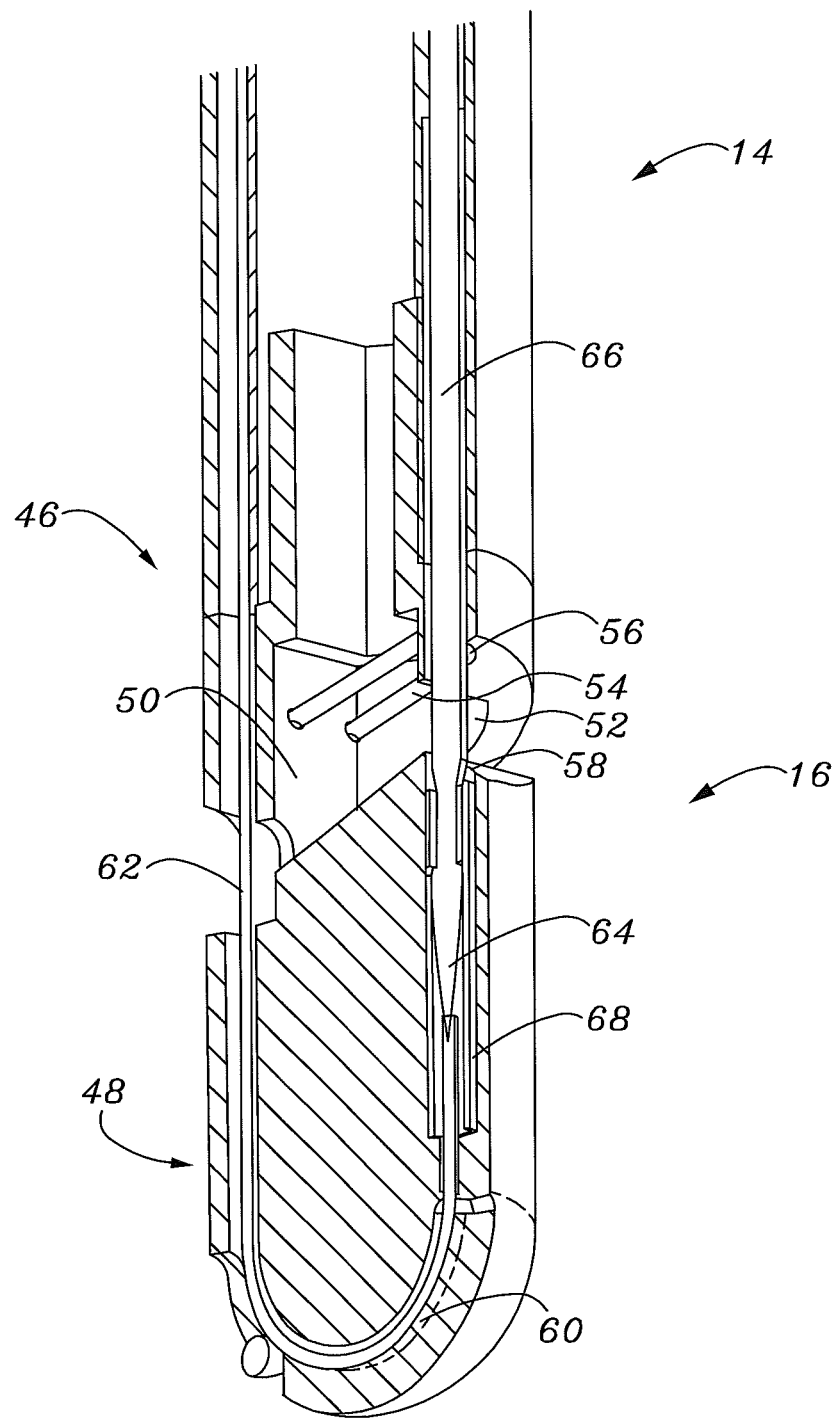
FIG. 8 shows a cross-sectional view of the engagement tip of the mitral valve repair device of the present invention in a retracted position wherein the deployable needle is deployed.
Figure 9:
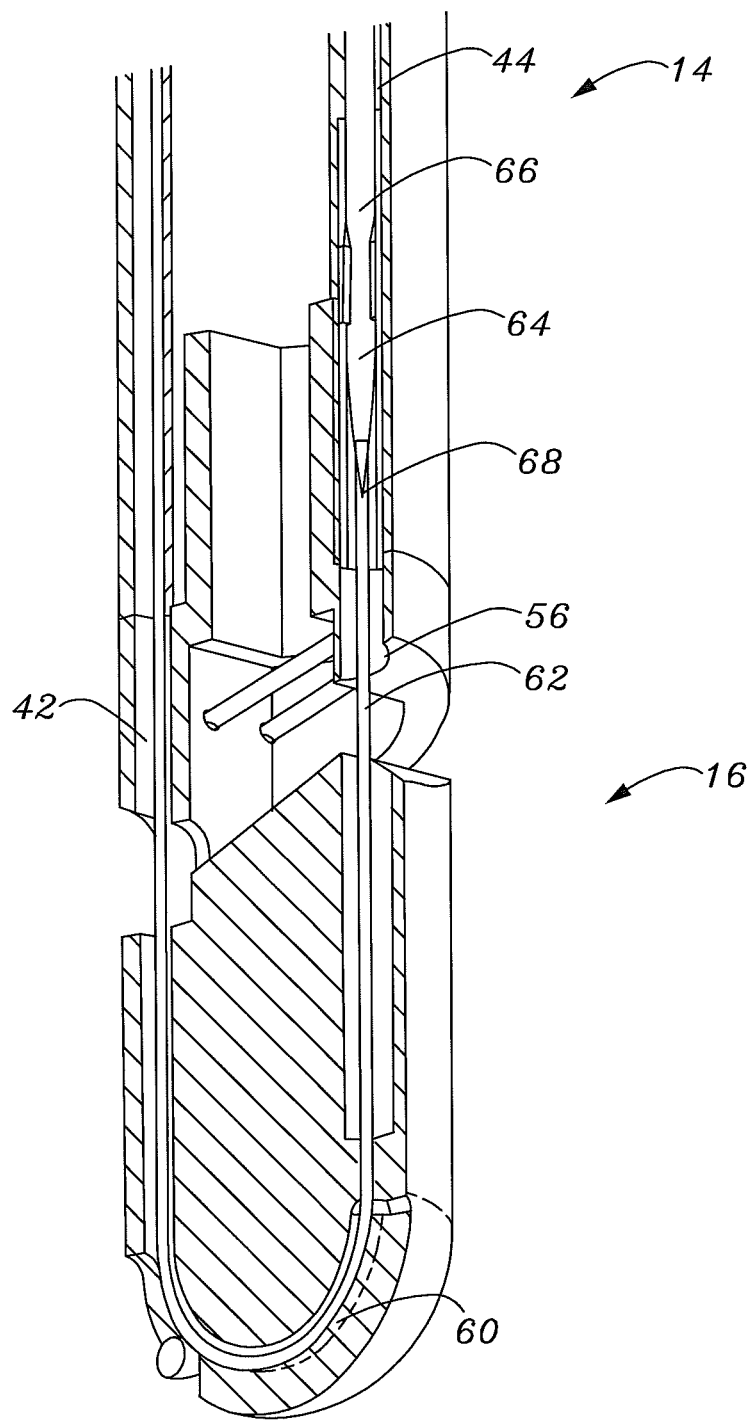
FIG. 9 shows a cross-sectional view of the engagement tip of the mitral valve repair device of the present invention in a retracted position wherein the deployable needle is retracted and is engaging a needle catch.

FIGS. 8 and 9 show cross sectional views of the engagement tip 16 of the present invention during use wherein a mechanical stabilization force may be applied to captured tissue. FIG. 8 shows a cross sectional view of the engagement tip 16 wherein the deployable needle 64 has been deployed from the fastener deployment port 56 located on the fastener deployment housing 46 through the fastener receiver port 58 and into the extendable tip 48. The deployable needle 64 is attached to the deployment housing 66 positioned within the one or more fastener lumens 44 of the elongated body 14. The deployment housing 66 is coupled to the fastener deployment actuator 24 positioned on the handle 12. To deploy the deployable needle 64, the user advances the fastener deployment actuator 24 on the handle 12 towards the stationary handle body 20, which results in the longitudinal movement of the deployment housing 66 within the fastener lumen 44 of the elongated body 14. Longitudinal movement of the deployment housing 66 results in the deployable needle 64 advancing through the fastener deployment port 56 into the fastener receiving port 58 and engaging the needle catch 68 located therein. As shown in FIG. 8, the deployable needle 64 has engaged the needle catch 68. The needle catch 68 is attached to the fastener material 62 located within the auxiliary lumen 42.

FIG. 9 shows a cross sectional view of the engagement tip 16 of the present invention wherein the deployable needle 64, having engaged and been retained by the needle catch 68 attached to the fastener material 62, is positioned within the fastener lumen 44 of the elongated body 14. To retract the deployable needle, the user moves the fastener deployment actuator 24 rearwardly away from the stationary handle body 20. As a result, the deployment housing 66 moves in a reward longitudinal motion which results in the deployable needle 64, which is attached to the deployment housing 66, moving rearwardly. The deployable needle 64, having the needle catch 68 and the fastener material 62 attached thereto, retracts through the fastener receiving port 58 and enters the fastener deployment port 56. As shown in FIG. 9, the fastener material 62 is in communication with the auxiliary lumen 42 and the fastener lumen 44, thereby traversing the actuation flange 50. In an alternate embodiment of the present invention the extendable tip 48, the fastener deployment housing 46, or the elongated body 14 may include at least one guidewire retaining device or lumen therein or attach thereto. In yet another alternate embodiment, the positions of the needles and needle catch are reversed (i.e. the needle moves from the extendable tip 48 to engage the needle catch in the port 56).

The present invention also discloses a method of using the single catheter mitral valve repair device of the present invention to repair discreet tissue portions in vivo. The description below describes a method of repairing dysfunctional heart valves, however, those skilled in the art will appreciate that the present invention may be adapted for use in other tissue repair procedures.

To repair a dysfunctional or otherwise incompetent heart valve, a guidewire capable of traversing the circulatory system and entering the heart of the patient is introduced into the patient through an endoluminal entry point. For example, an endoluminal entry point may be formed in a femoral vein or right jugular vein of a patient. Thereafter, the guidewire may be introduced into the patient through the endoluminal entry point and advanced through the circulatory system, eventually arriving at the heart. Upon arriving at the heart, the guidewire is directed into the right atrium of the heart, traverses the right atrium and is made to puncture the atrial septum, thereby entering the left atrium. The guidewire may then be advanced through the mitral valve while the heart is in diastole and traverses the left ventricle. The guidewire traverses the aortic valve into the aorta and is made to emerge from the left femoral artery through an endoluminal exit point. This methodology of positioning a guidewire is known to physicians skilled in the art of interventional cardiology. Once the guidewire is positioned, the endoluminal entry or exit port is dilated to permit entry of a catheter therethrough. A protective sheath may be advanced in the venous area to protect the vascular structure.

Figure 10:
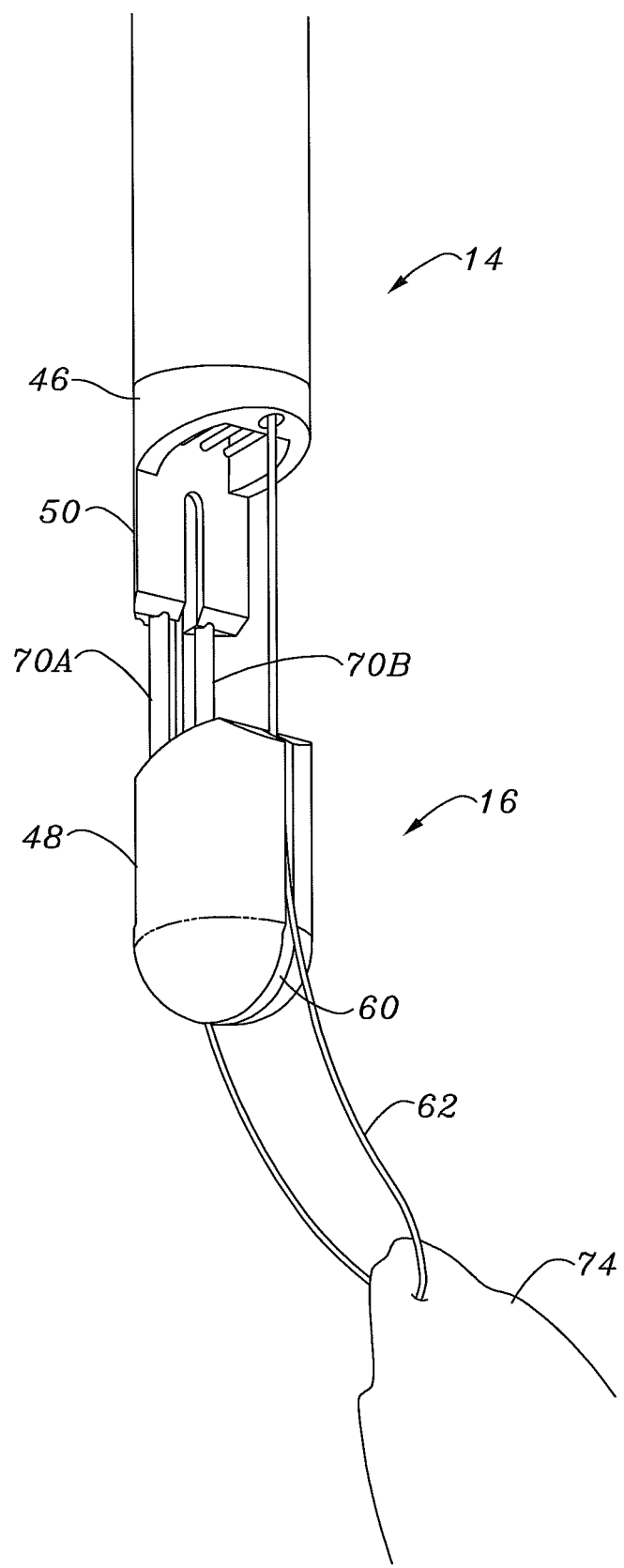
FIG. 10 shows a perspective view of the mitral valve repair device of the present invention having attached fastener material to a first tissue portion.

With the guidewire suitably anchored, the distal portion of the mitral valve repair device of the present invention may be attached to the guidewire. Thereafter, the elongated body 14 having the engagement tip 16 attached thereto is advanced through the dilated guidewire entry port to a point proximate the cusp portion of the mitral valve. Those skilled in the art will appreciate that the mitral valve repair device 10 of the present invention may approach the cusp of the mitral valve from an antegrade position or from a retrograde position as desired by the user. For a retrograde approach, the user attaches the repair device 10 to the guidewire emerging from the left femoral artery. The device is then advanced along the guidewire to a position proximate the retrograde aspect of the mitral valve. The engagement tip 16 of the mitral valve repair device 10 may be positioned proximate the tissue portion 72 of the mitral valve. Once suitably positioned, the tip actuator 22 positioned on the handle 12 may be actuated, thereby resulting in the extendable tip 48 of the engagement tip 16 extending distally from the fastener deployment housing 46. Thereafter, an external vacuum source (not shown) may be activated to apply a vacuum force to the mitral valve repair device 10 through the vacuum connector 18. The external vacuum source (not shown) communicates with the vacuum port 52 located on the engagement tip 16 through the at least one vacuum lumen 36 in the elongated body 14. With the extendable tip 48 distally extended from the fastener deployment housing 46, the tissue portion 72 located proximate to the vacuum port 52 is grasped and retained by the vacuum force applied by the external vacuum source (not shown). Once the tissue portion 72 is captured by the vacuum force supplied through the vacuum port 52, the tip actuator 22 located on the handle 12 is actuated to retract the extendable tip 48 toward the fastener deployment housing 46 thereby mechanically retaining and stabilizing the tissue portion 72 therebetween. Once the tissue is sufficiently stabilized, the fastener deployment actuator 24 located on the handle 12 may be actuated to deploy a fastening device through the tissue portion 72. To deploy the fastener device the user advances the fastener deployment actuator 24 toward the handle flange 28 positioned on the stationary handle body 20 of the handle 12, thereby causing the deployable needle 64 to exit the deployment port 56 and traverse the tissue positioned within the actuation flange 50. Thereafter, the deployable needle 64 enters the receiver port 58 formed on the extendable tip 48 and engages the needle catch 68 which is attached to the fastener material 62 positioned within the fastener channel 60. The fastener deployment housing 46 is returned to a non-deployed position by the user, thereby resulting in the deployable needle 64, which has retained the needle catch 68 attached to the fastener material 60, returning to a non-deployed position within the fastener lumen 44 of the elongated body 14, and resulting in the tissue portion 72 having fastener material 62 positioned therethrough. As shown in FIG. 10, with the fastener material 62 positioned through the tissue portion 72, the external vacuum source may be deactivated which results in the release of the captured tissue portion 72. Thereafter, the mitral valve repair device 10 of the present invention is removed from the patient's body leaving a fastener material 62 attached to the tissue portion 72.

Figure 11:
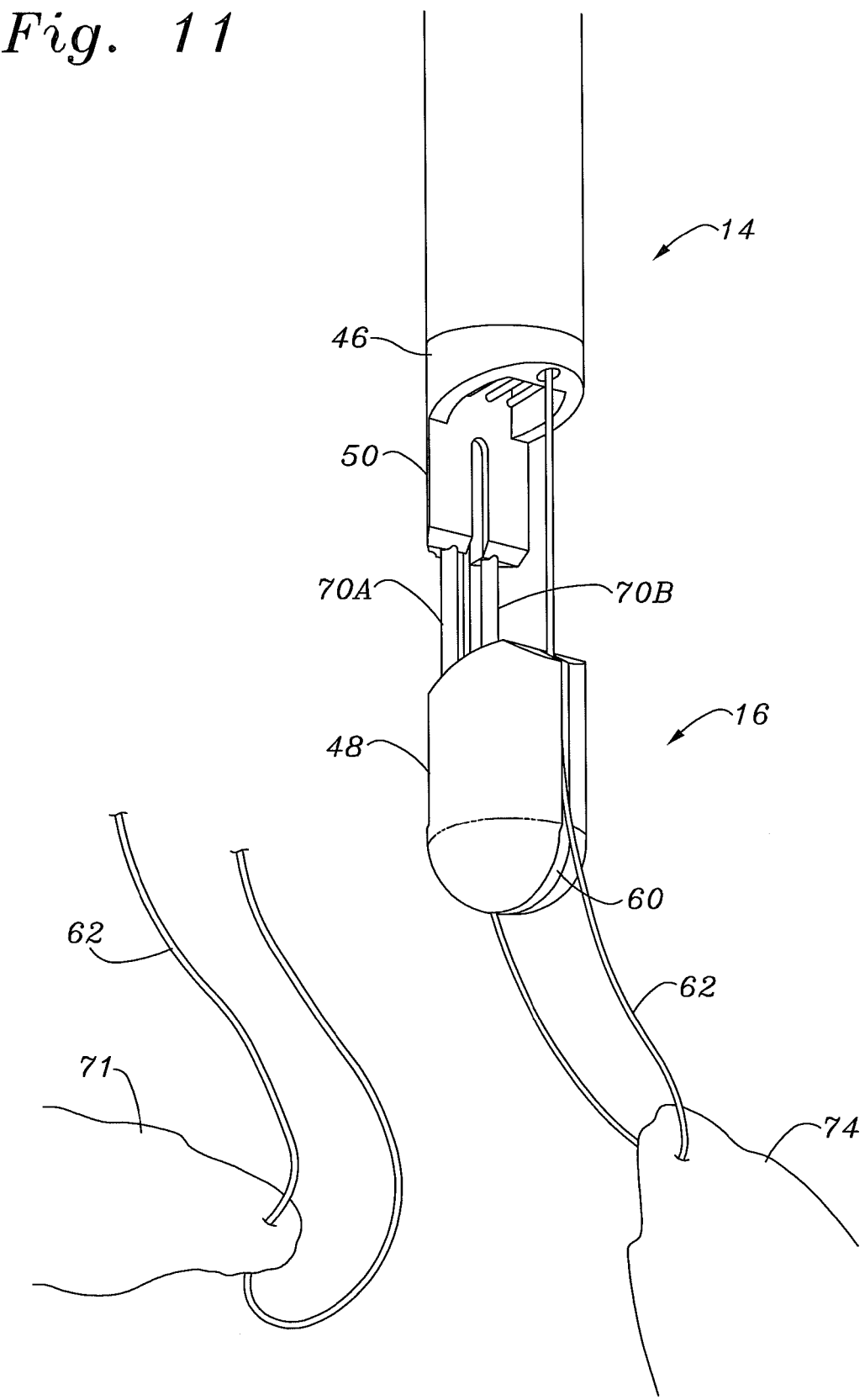
FIG. 11 shows a perspective view of the mitral valve repair device of the present invention having attached fastener material to a second tissue portion.
Figure 12:
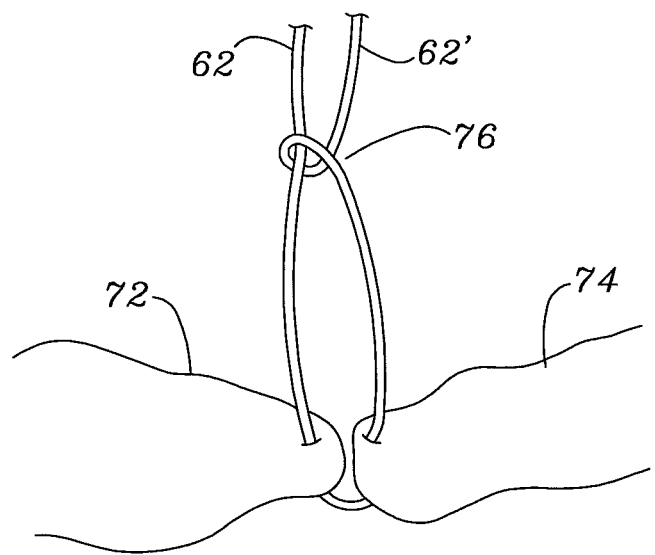
FIG. 12 shows a perspective view of discreet tissue portions having fastener material positioned therethrough.
Figure 13:
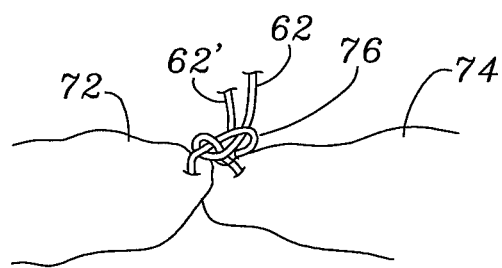
FIG. 13 shows a perspective view of discreet tissue portions being coapted with fastener material.

Once removed from the body of the patient, the mitral valve repair device 10 may be reloaded with deployable need and fastener material, rotated, and reintroduced into the patient thereby permitting the device to apply additional tissue fasteners to bodily tissue adjacent that already fastened. At least the distal portion of the mitral valve repair device of the present invention is re-attached to the guidewire. Thereafter, the elongated body 14 having the engagement tip 16 attached thereto is again advanced through the dilated guidewire entry port to a point proximate the cusp portion of the mitral valve. The engagement tip 16 of the mitral valve repair device 10 may be positioned proximate to another tissue portion 74 of the mitral valve. The preceding process is then repeated to secure suture material 62' to tissue portion 74. FIG. 11 shows the mitral valve repair device 10 positioned proximate to a second tissue portion 74 located near the first tissue portion 72. As shown, the fastener material 62' is positioned through the tissue portion 74 and the external vacuum source may be deactivated which results in the release of the captured tissue portion 74. Thereafter, the mitral valve repair device 10 of the present invention is removed from the patient's body and may be removed from the patient's body leaving a fastener material 62' attached to the tissue portion 74. Thereafter, the fastener material portions 62, 62' may be joined to coapt the individual tissue portions 72, 74. As shown in FIG. 12-13, a knot 76 is formed in the fastener material 62, 62' and advanced to the tissue portions 72, 74. In one embodiment, the knot 76 is formed external the patient's body and advanced to the repair site with a knot-pushing device.

Figure 5B:
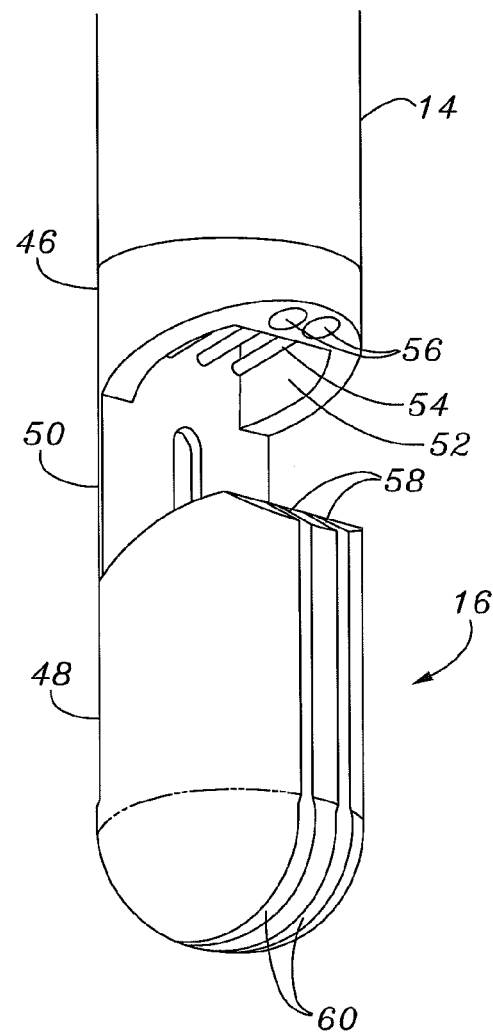

In the alternative embodiments of FIGS. 4B, 5B and 7B, the repair device need not be removed from the patient between the steps of securing the first and second tissue pieces. The dual fastening system of these alternate embodiments permits the faster material to be placed sequentially in both pieces of tissue simply by rotating the device after securing the first piece of tissue. Lastly, one of skill in the art will understand that if the vacuum source is strong enough, and the needle 64 sharp enough, extendable tip 64 need not translate relative to the deployment housing 46 to mechanically hold the tissue in place. The pieces of tissue can be held together in place with vacuum and punctured without use of mechanical retention.

In closing, it is understood that the embodiments of the invention disclosed herein are illustrative of the principals of the invention. Other modifications may be employed which are within the scope of the present invention. Accordingly, the present invention is not limited to that precisely as shown and described in the present disclosure.

What is claimed is:

1. A method of repairing a human heart, the method comprising:
providing a catheter having a proximal portion and a distal portion, wherein the distal portion comprises a distal portion main body and an extendable engagement tip, wherein the distal portion main body has a width, wherein the extendable engagement tip is telescopically connected to the distal portion main body by a sliding connecting rod, wherein the sliding connecting rod is connected to the distal portion main body at a first side of the distal portion main body and wherein the sliding connecting rod is radially displaced away from a central longitudinal axis of the elongated body, wherein the extendable tip is configured to be telescopically and distally extended away from and retracted back towards the distal portion main body, and wherein the elongate body distal portion has an open configuration and a closed configuration, wherein in the closed configuration the extendable tip is positioned against the distal portion main body, and in the open configuration the extendable tip is telescopically extended distally away from the distal portion main body to create a tissue-receiving opening bordered by the extendable tip, connecting rod, and distal portion main body, wherein the tissue-receiving opening is open on a second side of the elongate body distal portion and closed on the first side of the elongate distal body portion, wherein the second side of the elongate body distal portion is generally opposite to the first side of the elongate body distal portion, and the tissue-receiving opening extends across most of the width of the elongate body distal portion, across the central longitudinal axis of the elongated body, and from the second side of the main body distal portion to the connecting rod, wherein the catheter distal portion further comprises a first tissue fastener;

advancing the catheter distal portion into the heart;

positioning the catheter distal portion at a position adjacent a first heart tissue portion;

extending the extendable engagement tip away from the distal portion main body to thereby form the tissue-receiving opening;

positioning the first heart tissue portion within the tissue-receiving opening;

retracting the extendable engagement tip toward the distal portion main body to thereby grasp the first heart tissue portion between the extendable engagement tip and the distal portion main body;

deploying the first tissue fastener into the first heart tissue portion; and re-extending the extendable engagement tip away from the distal portion main body to thereby release the first heart tissue portion, wherein said re-extending the extendable engagement tip away from the distal portion main body occurs after advancing the first suture line through deployment of the first tissue fastener into the first heart tissue portion.

2. The method of claim 1, comprising:

deploying a second tissue fastener into a second heart tissue portion.

3. The method of claim 2, wherein the first tissue fastener comprises a first suture portion, the second tissue fastener comprises a second suture portion, and the first and second suture portions comprise portions of a common suture line, and wherein the method further comprises:

tightening the common suture line to secure the first heart tissue portion to the second heart tissue portion via the common suture line.

4. The method of claim 2, further comprising:

coapting the first heart tissue portion and the second heart tissue portion by drawing together the first and second tissue fasteners until the first heart tissue portion is in contact with the second heart tissue portion.

5. The method of claim 1, wherein the first tissue fastener comprises a first suture portion, the catheter distal portion comprises a first needle and a first needle catch, wherein the first needle catch is secured to the first suture portion, and the first needle catch is configured to be secured to the first needle when the first needle engages against the first needle catch, and wherein deploying the first tissue fastener into the first heart tissue portion comprises advancing the first needle through the first heart tissue portion, engaging the first needle against the first needle catch to thereby secure the first needle catch to the first needle, and retracting the first needle, with the first needle catch secured thereto, back through the first heart tissue portion to thereby pull the first needle catch and first suture portion through the first heart tissue portion.

6. The method of claim 5, wherein the catheter further comprises a second tissue fastener, wherein the second tissue fastener comprises a second suture portion, the catheter distal portion comprises a second needle and a second needle catch, wherein the second needle catch is secured to the second suture portion, and the second needle catch is configured to be secured to the second needle when the second needle engages against the second needle catch, wherein the method further comprises:

positioning the catheter distal portion at a position adjacent a second heart tissue portion;

extending the extendable engagement tip away from the distal portion main body to thereby form the tissue-receiving opening;

positioning the second heart tissue portion within the tissue-receiving opening;

retracting the extendable engagement tip toward the distal portion main body to thereby grasp the second heart tissue portion between the extendable engagement tip and the distal portion main body;

deploying the second tissue fastener into the second heart tissue portion by advancing the second needle through the second heart tissue portion, engaging the second needle against the second needle catch to thereby secure the second needle catch to the second needle, and retracting the second needle, with the second needle catch secured thereto, back through the second heart tissue portion to thereby pull the second needle catch and second suture portion through the second heart tissue portion; and re-extending the extendable engagement tip away from the distal portion main body to thereby release the second heart tissue portion, wherein said re-extending the extendable engagement tip away from the distal portion main body occurs after advancing the second suture line through deployment of the second tissue fastener into the second heart tissue portion.

7. The method of claim 6, wherein positioning the catheter distal portion at a position adjacent a second heart tissue portion comprises rotating the catheter after securing the first heart tissue portion.

8. A method of securing suture to heart tissue, the method comprising:

advancing a catheter into the heart, the catheter having a generally cylindrical elongated body having a proximal end and a distal end and a longitudinal axis, an extendable engagement tip capable of moving in telescopic relation to the elongated body distal end, an extendable support slidingly extending from the elongated body distal end at a first side thereof, wherein the extendable support is radially displaced away from the longitudinal axis of the elongated body, wherein the extendable engagement tip is secured to the extendable support, wherein when the extendable support is slidingly extended from the elongated body distal end, a tissue-receiving opening is formed which is defined by the elongated body distal end, the extendable engagement tip, and the extendable support, and wherein the tissue-receiving opening extends from the extendable support at the first side of the elongated body distal end, across the longitudinal axis of the elongated body, and to a second side of the elongated body distal end, wherein the second side of the elongate body distal end is radially opposite to the first side of the elongate body distal end, the catheter further comprising a first suture portion and a first needle;

advancing the elongate body distal end to a position adjacent a first heart tissue portion within the heart;

extending the extendable engagement tip and the extendable support distally of the elongate body distal end to thereby create the tissue-receiving opening;

positioning the first heart tissue portion within the tissue-receiving opening;

retracting the extendable engagement tip and the extendable support back toward the elongate body distal end to thereby mechanically retain and stabilize the first heart tissue portion;

passing the first needle through the first heart tissue portion, wherein the first suture portion is pulled through the first heart tissue portion by the first needle;

releasing the first heart tissue portion by extending the extendable engagement tip and the extendable support distally from the elongate body distal end; and withdrawing the catheter from the heart.

9. The method of claim 8, further comprising:

passing a second suture portion through a second heart tissue portion, wherein the first suture portion and the second suture portion are portions of a single suture line.

10. The method of claim 9, further comprising:

coapting the first heart tissue portion and the second heart tissue portion by drawing together the first and second suture portions until the first heart tissue portion is in contact with the second heart tissue portion.

11. The method of claim 10, further comprising:

forming a knot in the first and second suture portions.

12. The method of claim 8, wherein the catheter further includes a second needle and a second suture portion, the method further comprising:

after releasing the first heart tissue portion but before withdrawing the catheter from the heart, positioning the elongate body distal end adjacent a second heart tissue portion;

positioning the second heart tissue portion within the tissue-receiving opening;

retracting the extendable engagement tip and the extendable support back toward the elongate body distal end to thereby mechanically retain and stabilize the second heart tissue portion;

passing the second needle through the second heart tissue portion, wherein the second suture portion is pulled through the second heart tissue portion by the second needle; and releasing the second heart tissue portion by extending the extendable engagement tip and the extendable support distally from the elongate body distal end.

13. The method of claim 12, wherein positioning the elongate body distal end adjacent the second heart tissue portion comprises rotating the catheter.

14. A method of repairing a human heart, comprising:

providing a catheter comprising:

a main catheter body distal portion having a width and a distal end and a central longitudinal axis, the distal end having a first side and a second side, wherein the first side is on an opposite side of the central longitudinal axis from the second side, the distal end having a generally circular shape;

a main catheter body proximal portion;

an extendable engagement tip at the main catheter body distal portion, the extendable engagement tip configured to extend distally from the main catheter body distal portion to thereby form a tissue-receiving recess between the main catheter body distal portion and the extendable engagement tip, wherein the extendable engagement tip comprises a proximal end having a generally circular shape which matches the shape of the distal end of the main catheter body;

an extendable support configured to distally extend from the distal end of the main catheter body from a position adjacent the first side of the distal end of the main catheter body, wherein the extendable support is positioned radially away from the central longitudinal axis of the main catheter body distal portion and radially away from a central axis of the extendable engagement tip, the extendable support having a distal end with the extendable engagement tip positioned thereon, whereby when the extendable engagement tip is extended distally, the tissue-receiving recess between the main catheter body distal portion and the extendable tip extends across the entire width of the main catheter body distal portion except for the area at the first side of the distal end of the main catheter body, and wherein the tissue-receiving recess extends across the central longitudinal axis of the main catheter body distal portion;

a first tissue fastener positioned at or adjacent the main catheter body distal end and configured to be advanced across the tissue-receiving recess between the main catheter body distal portion and the extendable engagement tip; and an actuation device positioned at the main catheter body proximal portion, wherein the actuation device is configured to selectively extend and retract the extendable engagement tip from the main catheter body distal portion;

advancing the main catheter body distal portion to a position wherein the distal end thereof is within the heart adjacent a first tissue portion;

activating the actuation device to extend the extendable engagement tip distally from the main catheter body distal portion to thereby form the tissue-receiving recess;

positioning the first tissue portion within the tissue-receiving recess;

retaining and stabilizing the first tissue portion by retracting the extendable engagement tip toward the main catheter body distal portion to thereby mechanically hold the first tissue portion between the extendable engagement tip and the main catheter body;

advancing the first tissue fastener across the tissue-receiving recess between the main catheter body distal portion and the extendable engagement tip, whereby the first tissue fastener passes through the first tissue portion; and releasing the first tissue portion from the main catheter body by extending the extendable engagement tip distally from the main catheter body distal portion.

15. The method of claim 14, wherein the catheter comprises a second tissue fastener positioned at or adjacent the main catheter body distal end and configured to be advanced across the tissue-receiving recess between the main catheter body distal portion and the extendable engagement tip, the method further comprising:

after releasing the first tissue portion from the main catheter body, positioning the main catheter body distal portion with the distal end thereof adjacent a second tissue portion;

positioning the second tissue portion within the tissue-receiving recess;

retaining and stabilizing the second tissue portion by retracting the extendable engagement tip toward the main catheter body distal portion to thereby mechanically hold the second tissue portion between the extendable engagement tip and the main catheter body;

advancing the second tissue fastener across the tissue-receiving recess between the main catheter body distal portion and the extendable engagement tip, whereby the second tissue fastener passes through the second tissue portion;

releasing the second tissue portion from the main catheter body by extending the extendable engagement tip distally from the main catheter body distal portion; and withdrawing the catheter from the heart.

16. The method of claim 15, wherein positioning the main catheter body distal portion with the distal end thereof adjacent the second tissue portion comprises rotating the catheter.

17. The method of claim 15, wherein the first tissue fastener comprises a first suture portion, the second tissue fastener comprises a second suture portion, the catheter comprises a first suture needle positioned at or adjacent the main catheter body distal end and configured to be advanced across the tissue-receiving recess between the main catheter body distal portion and the extendable engagement tip and to thereby pull the first suture portion across the tissue-receiving recess, the catheter comprises a second suture needle positioned at or adjacent the main catheter body distal end and configured to be advanced across the tissue-receiving recess between the main catheter body distal portion and the extendable engagement tip and to thereby pull the second suture portion across the tissue-receiving recess, wherein the first suture portion and the second suture portion are portions of a single suture line, and wherein advancing the first tissue fastener across the tissue-receiving recess comprises advancing the first suture needle across the tissue-receiving recess, and advancing the second tissue fastener across the tissue-receiving recess comprises advancing the second suture needle across the tissue-receiving recess.

18. The method of claim 14, wherein the first tissue fastener comprises a first suture portion, the catheter comprises a first suture needle positioned at or adjacent the main catheter body distal end and configured to be advanced across the tissue-receiving recess between the main catheter body distal portion and the extendable engagement tip and to thereby pull the first suture portion across the tissue-receiving recess, and wherein advancing the first tissue fastener across the tissue-receiving recess comprises advancing the first suture needle across the tissue-receiving recess.

* * * * *